United States Patent [19]

Enderlin et al.

[11] Patent Number: 4,843,879
[45] Date of Patent: Jul. 4, 1989

[54] APPARATUS FOR AUTOMATIC QUALITY CONTROL OF TEXTILE THREADS

[75] Inventors: Robert Enderlin, Morschwiller; Richard A. Schutz, Mulhouse; Jean-Yves Drean, Brunstatt, all of France

[73] Assignee: Superba S. A., France

[21] Appl. No.: 104,597

[22] Filed: Sep. 29, 1987

Related U.S. Application Data

[63] Continuation of Ser. No. 890,980, Jul. 25, 1986, abandoned, which is a continuation of Ser. No. 622,228, Jun. 19, 1984, abandoned.

[30] Foreign Application Priority Data

Jun. 21, 1983 [FR] France .................. 83/10360

[51] Int. Cl.[4] .................................. G01L 5/04
[52] U.S. Cl. ........................................... 73/100
[58] Field of Search ............... 73/159, 160, 831, 834, 73/847; 57/90, 352; 364/470, 468, 552, 550

[56] References Cited

U.S. PATENT DOCUMENTS

| | | | |
|---|---|---|---|
| 2,211,434 | 8/1940 | Perry | 57/90 |
| 3,731,069 | 5/1973 | Goto et al. | 73/160 |
| 3,751,981 | 8/1973 | Jernigan et al. | |
| 3,788,138 | 1/1974 | Heusser | |
| 3,919,886 | 11/1975 | Chambley | 73/160 |
| 4,030,082 | 6/1977 | Goto | 73/160 |
| 4,045,659 | 8/1977 | Agagawa et al. | 73/160 |
| 4,084,434 | 4/1978 | Goodrich et al. | 73/160 |
| 4,116,393 | 9/1978 | Inouye et al. | 73/160 |
| 4,173,787 | 11/1979 | Katona et al. | 73/160 |
| 4,295,360 | 10/1981 | Fountain | 73/160 |
| 4,584,875 | 4/1986 | Woo et al. | 73/160 |

FOREIGN PATENT DOCUMENTS

| 693136 | 6/1953 | Switzerland | 73/160 |
|---|---|---|---|
| 888576 | 1/1962 | United Kingdom . | |

OTHER PUBLICATIONS

Hartsuch, Intro. to Textile Chemistry, Copy 1950, p. 113, John Wiley & Sons, Inc., N.Y.

Primary Examiner—Stewart J. Levy
Assistant Examiner—Robert R. Raevis
Attorney, Agent, or Firm—Davis, Bujold & Streck

[57] ABSTRACT

The present invention concerns a method and an apparatus for quality control of textile threads, and particularly of threads produced by different spinning methods. The apparatus comprises a housing (10) containing two measurement modules. A first module comprises a double condenser (32) and its associated electronic circuit to determine uniformity of linear mass of the thread, a precision scale (31) to determine linear mass and a drive means (33). The second module comprises a device (34) and a device (37) which cooperate to determine twist and elastic recovery of the thread. A manipulator (17) allows automatic positioning of the test pieces of thread (46) admitted into the apparatus through flexible tubes (16). The apparatus offers the advantage of permitting a series of measurements to be taken and computer processed for purposes of statistical compilation and/or memory storage.

13 Claims, 4 Drawing Sheets

APPARATUS FOR AUTOMATIC QUALITY CONTROL OF TEXTILE THREADS

This is a continuation of co-pending application Ser. No. 890,980, filed on July 25, 1986, which is a continuation of 622,228, filed June 19, 1984, both now abandoned.

The present invention concerns a method for automatic quality control of textile thread and an apparatus for implementing the method.

Controlling textile thread quality is more and more necessary, especially since the advent of thread production using different spinning methods, such as the traditional continuous ring spinning frame or free-fiber end spinning method, and variations of these methods. Actually, the appearance, performance during mechanical operations and during dyeing of thread made by these different spinning methods, even in the case of identical fibers, may all vary significantly, thereby limiting use of the thread to one specific finished item. In other words, the same threads made from the same primary materials but resulting from different spinning methods, when woven into one piece of fabric or knitted material, will cause defects in appearance such as slubs and other flaws rendering them unsalable. Moreover, the fabric manufacturer frequently does not himself produce all the threads he uses.

Generally, speaking, threads manufactured according to the traditional continuous ring spinning frame method are sufficiently uniform in structure that simply controlling strength and linear mass uniformity prevents manufacturing problems during weaving and knitting, even though differences in twist, if significant enough, may cause certain defects.

With today's market supplying thread manufactured by various methods, control of strength and uniformity of strength, i.e., uniformity of linear mass, is inadequate in preventing defects. Moreover, although they may be similar with respect to strength, uniformity and twist, threads spun by the free-fiber end method differ in structure from those produced by the traditional method. Yet, even threads having these same general characteristics, spun on different machines using the free-fiber end method, or even on the same machines but with different calibrations, degrees of wear and tear or of cleanliness, may have structures sufficiently different so as to cause the above-mentioned visual defects in fabric.

Some relatively recent studies, described particularly in the article entitled "De la torsion des files: notion, determination, application a la caracterisation de la structure et de l''aspect" by R. A. Schutz and J. Y. Drean, appearing in "l'Industrie Textile" No. 1089, May, 1979 pages 421–427; in the article "Charakterisierung der Garne, hinsichtlich ihrer Verarbeitung und Eigenschaften" by the same authors, published in "Melliand Textiberichte", August, 1979, pages 656–659 and in the article entitled "Charakterisierung der Garne" by R. A. Schutz, J. Y. Drean and D. Carriere, published in "Textilsveredlung", January, 1981, pages 9–11, have led to new methods for categorizing threads, particularly concerning threads manufactured by the free-fiber end method and allowing thread structure to be referenced mathematically.

Nevertheless, these traditional methods, tested in laboratory settings, have the drawback of being rather long and tedious. Actually, until now and for the reasons described above, each different phase of qualty control for thread has entailed using a separate device, notably a winding apparatus and a scale to determine quality in terms of weight (i.e., denier), a regulator to determine regularity, a torsion meter to determine twist and a dynamometer to determine elastic recovery.

Of the different types of devices available on the market, some have been automated to some extent, but remain limited in the degree of quality control they can attain. Furthermore, in view of the norms and restrictions involved with the methods used, it is necessary to establish certain data from other devices in order to take some of these measurements. Thus voltage determination, a prerequisite for certain types of measurements (twist, elastic recovery, etc.), must be applied as a function of denier, which must therefore be previously known or determined.

It being understood that, on the one hand, a particular type of determination proves less and less adequate for thread classification, and on the other hand, certain determinations are long and necessitate action and/or intervention by the operator, it seems important to think of quality control in other terms, i.e., according to an appropriate methodology and measurement system.

The present invention proposes to overcome the above-mentioned disadvantages and to provide the textile industry with a method for automatic quality control of textile threads, as well as with a simple, effective apparatus implementing this method, which effects a plurality of measurements allowing precise classification of threads, whatever their mode of manufacture.

To achieve this, the method for automatic quality control of textile threads according to the invention is characterized by the fact that using only one apparatus, it automatically takes a series of measurements for at least one test piece of thread, these measurements being designed to permit at least one determination of thread denier and one determination of linear mass regularity, and/or at least one determination of twist and one determination of elastic recovery, by the fact that these measurements are repeated on a series of test pieces of the same thread, by the fact that the results are recorded in a memory, and by the fact that these results are processed for statistical and/or storage purposes.

According to a preferred method, the measurements for determining denier and linear mass are taken at a first module for at least one test piece of thread, and at a second module the measurements for determining twist and elastic recovery are taken for at least one test piece of thread. These two measurements taken at two different modules preferably are carried out simultaneously for two different test pieces of the same or different threads.

To effect these measurements, a series of test pieces of thread is preferably introduced into the apparatus, in such a way that their extremities are each situated in a preliminary position from which they may be successively introduced into one of the measurement modules, a series of measurements is successively carried out for each thread by the measuring devices in the same module, and the series of measurements is stopped when a predetermined number of measurements has been taken, for example when statistical precision is attained for a number of measurements smaller than the said predetermined number.

Preferably, positioning of the test pieces of thread before the measurement phase is in part automatic by means of air jets introducing the test pieces into the control apparatus and in part manual by placing the free ends of the test pieces in their respectively preliminary positions inside the apparatus.

At the first point during the measurement phase, the extremities of the two test pieces of thread are sucessively automatically lifted from their respective preliminary positions and each introduced automatically into one of the two measurement modules.

Because of the specialized positioning of the measuring means, the test pieces are positioned vertically during the course of the measurements taken in each of the modules.

Furthermore, waste products and test pieces already measured are automatically discharged by suction.

The apparatus for automatic quality control of textile thread according to the invention is characterized by the fact that it comprises a case or housing containing at least two measurement modules, one provided with means for taking measurements to determine denier and/or uniformity of linear mass for at least one test piece of thread, the other with means for taking measurements to determine twist and/or elastic recovery for at least one test piece of thread, and by the fact that it also comprises means for automatically repeating these measurements on a series of test pieces of the same thread, means for recording the measurement results in memory and means for processing the data for purposes of statistical compilation and/or memory storage.

- According to one advantageous embodiment, the first module comprises a measuring means which by means of a circuit determines uniformity of thread denier, a measuring means for the thread denier and a drive means, these three components being disposed along the same vertical axis and disposed consecutively to determine thread quality and uniformity of quality.

The means for measuring uniformity of denier preferably comprises a double condenser having a central plate and two lateral plates defining two passageways, through one of which the thread to be tested passes, and an electronic control circuit connected to the condenser. This control circuit comprises an oscillator disposed to apply two alternating voltages in opposing phases to the lateral plates, an amplifier and a demodulator to detect variations in voltage upon the central plate, and a reverse-feedback circuit comprising an analog-digital convertor and a digital-analog convertor to accommodate disequilibrium arising from the connecting circuit comprising the plates of the double condenser, the demodulator being connected to a central processing unit for statistical processing and/or memory storage of results.

The drive means associated with the two measuring means for the first module preferably comprises a U-shaped bin attached to the mounting plate, a drive cylinder connected to a stepper drive motor and a pressure cylinder with an anti-slip surface, said pressure cylinder being equipped with means ensuring constant pressure of its peripheral surface upon the peripheral surface of the drive cylinder.

To facilitate automatic insertion of the thread between the pressure cylinder and the drive cylinder, the pressure cylinder has at least one groove disposed the axial length of its exterior periphery, and preferably has a series of juxtaposed axial grooves.

The means for denier measurement comprises, according to a preferred embodiment, a precision scale located on a flat extension integral with the lifting plate, provided with a receptacle for the lengths of thread subject to measurement and with an output means for the data corresponding to the successive measurements, said data being transmitted to a processing unit for statistical compilation and/or storage in memory.

The second module designed for measuring the degree of twist and elastic recovery for at least one test piece of thread comprises a stepper motor provided with a gripping means or forceps caused to rotate in either of two directions by said motor, and disposed to hold one extremity of the piece of thread to be tested, a device comprising a forceps, and an energy storage means and mechanical means for upwardly displacing said device along a vertical opening disposed in the lifting plate.

The mechanical means for upward displacement of this device comprises a stepper motor and a vertical screw connected for rotation by said motor, said screw being connected to the device to maintain its vertical displacement.

To avoid contamination of the apparatus by thread residue or by test pieces already measured, the apparatus preferably comprises means for automatically suctioning out the residue.

Moreover, to allow simultaneous treatment of two test pieces in the two measurement modules of the apparatus, there is preferably provided a deflector which defines two separate zones, one containing a thread test piece tested by the first module and the other containing a thread test piece tested by the second module.

Positioning the threads for measurement in either of the measuring modules is effected by means of a manipulator controlled by the central processing unit, and comprising a rotating disc, a guide block mounted on two rails perpendicularly affixed to said disc so that the block is slidable along these rails, a stem or shaft slidable within said guide block, a manipulating arm mounted at the free extremity of said stem and having a cutting forceps to lift the threads from their preliminary position and move them to the measuring means, and/or to cut the threads into predetermined lengths.

Finally, the apparatus advantageously comprises a toothed rack or rake, preferably mounted on the outside of the housing containing the measuring instruments, this rack comprising a chassis having a plurality of stems disposed to hold bobbins of thread to be tested, and suction tubes to suction the threads and thereby move them through the small flexible tubes inside the apparatus.

The present invention will be better understood with reference to the description of one example thereof made with reference to the attached drawings, in which.

Figure 1:
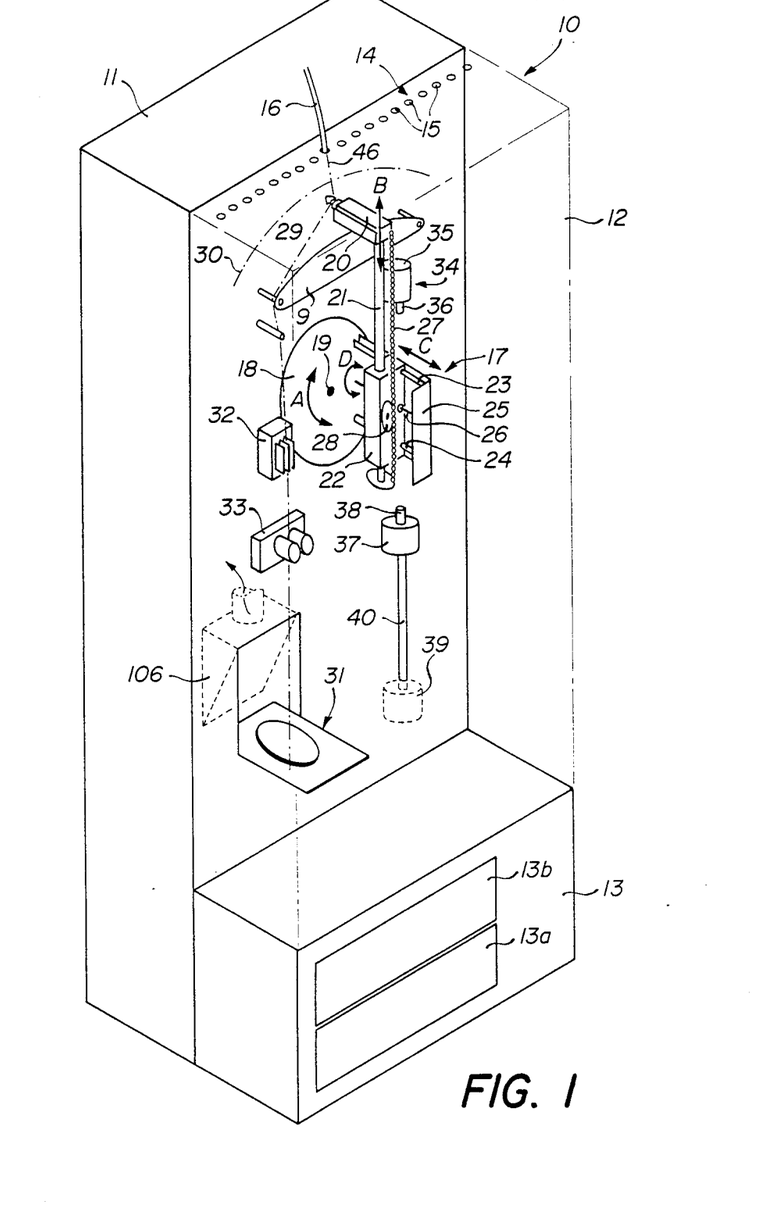
FIG. 1 is a schematic perspective of the automatic quality control apparatus according to the invention.

With reference to the drawings and particularly to FIG. 1, the apparatus shown comprises a casing or housing 10 containing a vertical lifting plate 11 serving as a support for the unit of measuring instruments, a frontal opening 12, preferably transparent, allowing the operator to access the measuring instruments, a base 13 containing the means 13a for controlling the drive means and the central processing unit 13b. A console (not shown) with a keyboard for data input and a cathode screen, known per se, are associated with the apparatus shown in FIG. 1. The housing 10 preferably is made of rigid material with metal or synthetic plates, and is mounted on the framework. However, this embodiment may be modified according to use, or as defined by the operator or manufacturer.

The upper plate 14 of housing 19 comprises a series of openings 15 in which there are flexible tubes 16 to move the test pieces of thread into the apparatus. These test pieces originate from a rack (shown in FIG. 2) in a manner which will be described in detail hereinafter. They penetrate tubes 16 and their ends are manually cut and positioned by appropriate forceps or gripping means described with reference to FIG. 3.

Vertical lifting plate 11 is provided with a manipulator 17 movable along three orthogonal axes, and electronically controlled. Manipulator 17 comprises a disc 18 which rotates in either direction of double arrow A around axle 19 supported by a platform (not shown) and mounted on the posterior surface of plate 11, and manipulating arm 20 perpendicularly attached to the free end of stem 21 movable in either direction of double arrow B. Stem 21 is supported by guide block 22, itself supported by two rails 23 and 24 mounted between disc 18 and angled support 25, also supported by this disc. Disc 18 is caused to rotate by a stepper drive motor (not shown) mounted on the posterior surface of plate 11. Displacement of guide block 22 in either direction of double arrow C by means of screw 26 propelled in an associated direction of double arrow D takes place by means of a stepper motor (not shown). Displacement of stem 21 takes place by virtue of a chain 27 suspended between the two extremities of the said stem and which meshes with a gear 28 caused to rotate in either of two opposing directions by a stepper motor (not shown), situated within or supported by guide block 22. The free end of manipulating arm 20 is provided with a forceps 29, the function of which is to grip and/or cut the pieces of thread to be tested. As it is not part of the object of the present invention, this forceps is not described in further detail in the disclosure.

Figure 3:
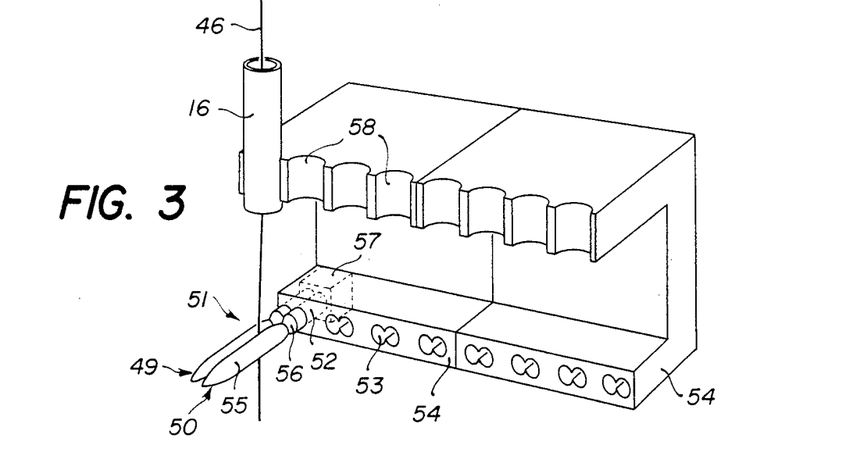
FIG. 3 is a perspective of the forceps for placing the test pieces of thread in their preliminary position inside the apparatus shown in FIG. 1.

The role of manipulator 17 is to lift the ends of the threads previously placed in the preliminary positions within the forceps shown in FIG. 3 which are disposed along an arc 30.

The first measuring module, vertically mounted on the left of the apparatus shown in FIG. 1, comprises a device for determining quality or linear mass, this device comprising a precision scale 32 described in more detail with reference to FIG. 6, a device to determine linear mass regularity consisting of a double condenser 32 and the circuit associated therewith, described in greater detail with reference to FIGS. 4 and 5, as well as a drive mechanism described in greater detail with reference to FIGS. 6 and 7.

The second measuring module, veritically mounted on the right of the apparatus shown in FIG. 1, comprises a device 34 consisting of a stepper driver motor 35 to cause rotation of forceps 36, disposed to grip an extremity of a thread test piece for which it is dsired to measure twist, and a device 37 also provided with a forceps 38 to hold the other extremity of the test piece for which it is desired to measure twist. Actually, device 37 is axially movable between the position shown by the solid line and position 39, shown by broken lines. Displacement of this device is possible because of a longitudinal opening 40 disposed in lifting plate 11. This device will be described in greater detail with reference to FIG. 9.

Figure 2:
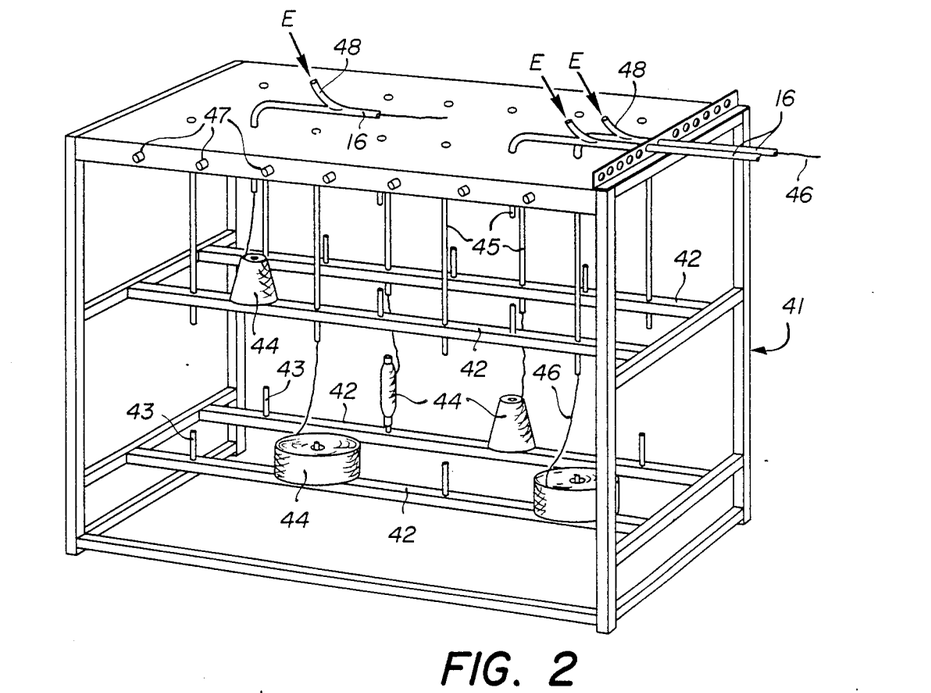
FIG. 2 is a schematic perspective of the rack holding a series of bobbins of thread to be tested.

As previously mentioned, the threads originate from a support term the rack and shown in FIG. 2, which is comprised of body 41, perhaps made of soldered metal sections. Body 41 has, in this instance, four cross pieces 42 each having a series of stems 43 upon which are respectively wound the bobbin 44 of thread to be tested. As shown in the drawing, the bobbins may vary considerably in size and shape and their number may vary considerably according to rack size. In practice, it is preferably to limit storage to as many as twenty-four bobbins of thread. Above each bobbin there is disposed a suction tube 45 in communication with one of the flexible tubes 16 terminating at the quality control apparatus. Compressed air for suctioning thread 46 which has been manually positioned at the entrance to corresponding suction tube 45 and for continuing on to housing 10, is laterally injected into tubes 16, as shown by arrows E. Suction is controlled by means of handles or levers 47 mounted on the upper cross piece of body 41. These levers control valves allowing communication between conduits 48, which tangentially inject compressed air into tubes 16, and a source of compressed air (not shown).

While not indispensable to the functioning of the quality control apparatus, the rack is a very useful accessory for automatic testing of a considerable number of different threads.

When the threads are injected above apparatus 10, an operator positions them between clamps 49 and 50 of forceps 51, shown in FIG. 3. Each forceps 51 comprises two clamps each having a cylindrical posterior portion 52 engaged in opening 53 of support 54, and an anterior bullet-like portion 55, the two portions being separated by a zone 56 of reduced diameter. The two clamps 49 and 50 forming piece 51 are disposed side-by-side, and each respectively engages, with a small amount of play, in two inter-communicating openings 53. A permanent magnet 57, situated in an appropriate opening disposed in support 54, which is made of anti-magnetic material such as aluminum or a synthetic, ensures auto-alignment of the two pieces 49 and 50 and locking thereof. A piece of thread 46 lead through conduit 16 situated within semi-cylindrical opening 58 in support 54 is gripped by clamps 49 and 50 of forceps 51 by virtue of the auto-aligning effect exerted by magnet 57 and of the play between cylindrical extremities 52 of these clamps and the openings 53 holding them. Each support 54 comprises four forceps 51. The unit of supports 54 is disposed in arc 30 of the apparatus as shown in FIG. 1.

When the threads are gripped by the clamps of forceps 51, they are then in preliminary position ready for manipulator 17 to assume its function and introduce them into the various measurement instruments.

Figure 4:
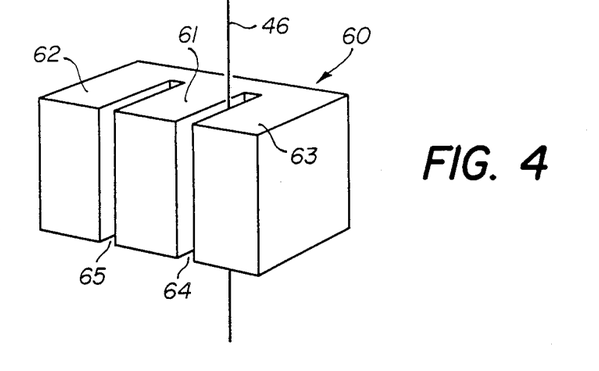
FIG. 4 is a schematic view of the means for measuring uniformity of linear mass mounted inside the apparatus of FIG. 1.

One of these measurement instruments is shown in FIG. 4. It consists of a double condenser connected to a measurement circuit shown in FIG. 5 for comparing the mass of predetermined lengths of thread (for example, 5 mm.) by means of capacitative measurement. To achieve this, double condenser 60 comprises central plate 61 and two lateral plates 62 and 63 defining two passageways 64 and 65. Passageway 64 contains only air, while passageway 65 contains thread 46.

Figure 5:
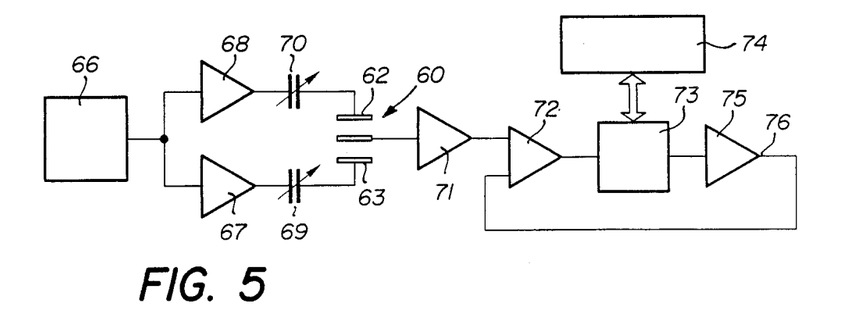
FIG. 5 is a schematic illustration showing in block form the circuit connected to the measuring means shown in FIG. 4.

As shown in FIG. 5, condenser 60 forms a part of the connecting circuit whose equilibrium is dependent upon the mass of thread in passageway 64. The circuit comprises an oscillator 66 connected to two amplifiers 67 and 68 disposed to provide signals in opposite phases to the two lateral plates 62 and 63. Two regulating condensers 69 and 70 allow the capacity of double condenser 60 to be adjusted while empty. When both charges of double condenser 60 are equal, no voltage registers on central plate 61. Conversely, if the two charges are different, the voltage on the central plate is amplified by amplifier 71, transmitted to one of the input means of analog/digital convertor 72, demodulated by demodulator 73 and transmitted to the central processing unit, consisting of micro-computer 74. In this way, measurements of uniformity in linear mass can be taken for a relatively long test piece, for example, 100 mm. and thereafter stored in memory and statistically compiled. A reverse-feedback circuit accommodating disequilibrium in the connecting circuit comprises a digital/analog convertor whose output means 76 is connected to the other input means of analog/digital convertor 72.

For these measurements to be taken, thread 46 must pass through opening 64 at a relatively high speed. Controlling speed of thread passage is a function of device 33 shown in detail in FIGS. 7 and 8.

This device comprises essentially a drive cylinder 80 and a pressure cylinder 81. Drive cylinder 80 is controlled by stepper motor 82, the speed of which is precisely controlled and which has a calibrated diameter, so that the length of the thread propelled by this device may be calculated with whatever degree of precision is necessary. The pressure cylinder is provided with an anti-slip surface 83 in contact with the peripheral surface of drive cylinder 80. The device comprises a U-shaped receptacle or bin 84 supported by lifting plate 11. Drive shaft 85 of motor 82 is housed in axial opening 86 of cylinder 80. The axis of the latter is, in addition, supported by a platform 87 situated inside an opening disposed in recovery plate 88 connected to receptacle 84 by screws 89. Cylinder 80 preferably comprises interior openings 90 to decrease inertia. Cylinder 81 has an axle 91 supported by two platforms 92 and 93. These two platforms are housed within sliding block 94 which is subject to the action of two springs 96 by means of two plugs or blocks 95, the compression of the springs being controlled by two regulating screws 97. Recovery plate 98 connected to receptacle 84 by screws 99 has the same protective function as plate 88. The exterior peripheral rim of pressure cylinder 81 is provided with a certain number of openings 100, the function of which is to allow thread 46 to automatically be introduced between cylinders 80 and 81 in a manner known per se.

Figure 6:
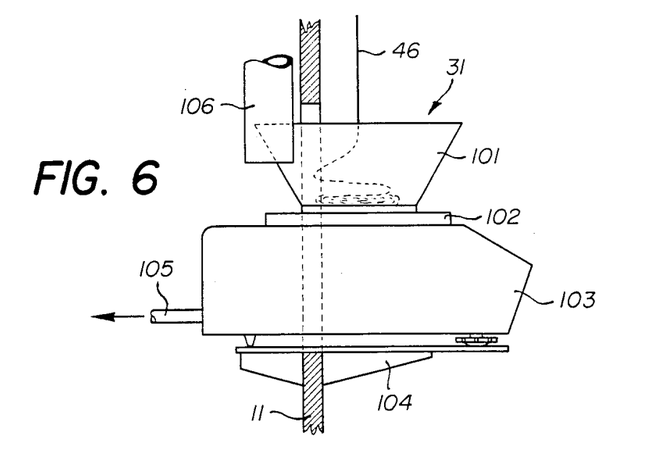
FIG. 6 is an elevational view of the precision scale of the measuring means which determines denier.

After passing through cylinders 80 and 81, thread 46 is deposited in receptacle 101 upon plate 102 of precision scale 103 shown in FIG. 6. This scale is supported by a flat extension 104 integral with lifting plate 11. The scale determines quantity, i.e., the linear mass of the thread, by weighing controlled lengths deposited in receptacle 101. Connector 105 transmits the results of the successive weighings to the central processor and/or memory for statistical compilation and/or memory storage.

Evacuation of pieces already tested is accomplished by suctioning them through a container or a suction tube 106.

The measurements of denier and uniformity of denier are obtained by the same module. The drive means is common to the two so-called measuring means. The thread is positioned vertically during the course of these measurements and is evacuated automatically after the tests.

The second module comprises, as previously mentioned, a means for determining the degree of twist in test pieces of thread and their elastic recovery. This determination implies prior testing and particularly, knowledge of denier from which previous voltage is determined. By virtue of electronic testing and control, measurement of denier may be completely automatized. This determination is effected by means of device 34 consisting of stepper motor 35 controlling the two directions of movement for forceps 36 which grips the test piece.

Figures 7, 8, 9:
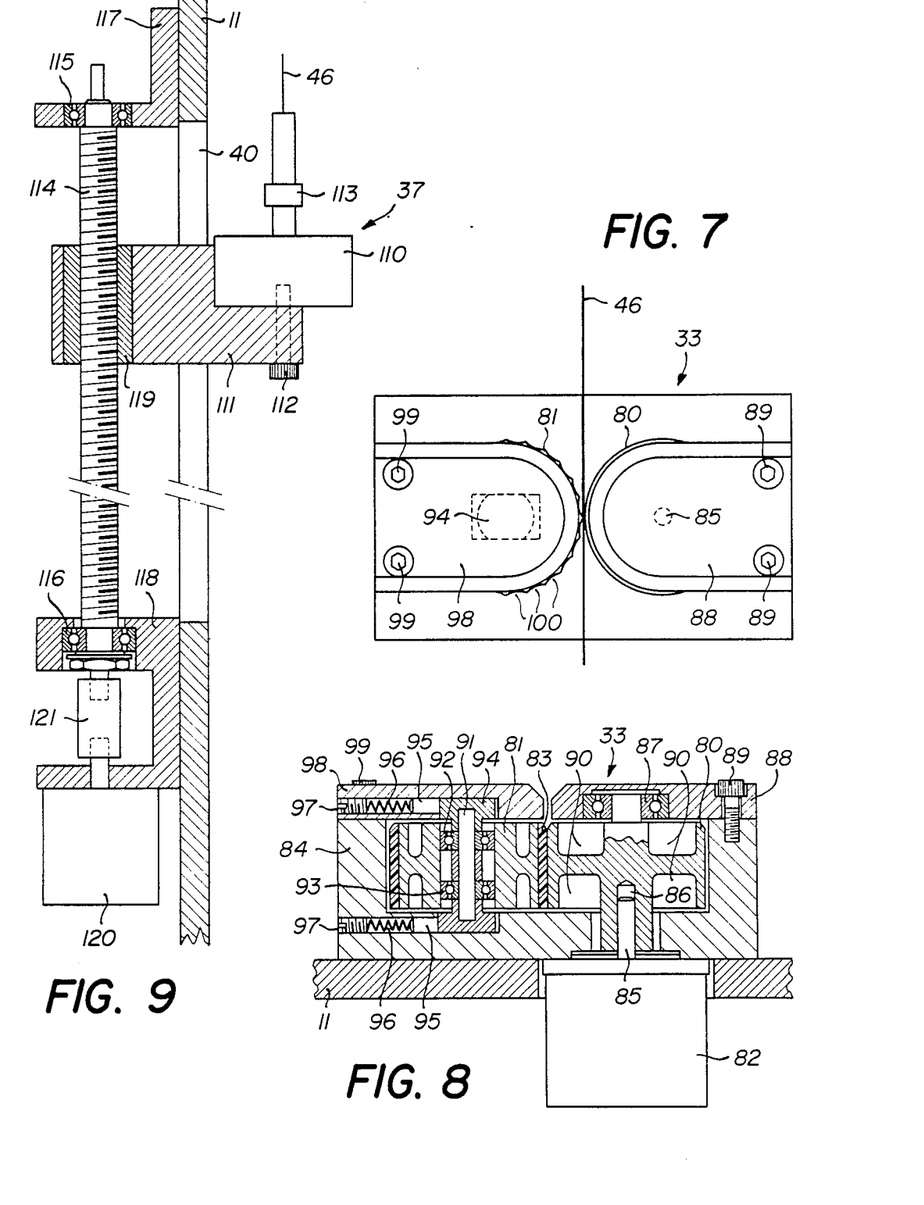
FIG. 7 is an elevational view of the drive means for the first measurement module.
FIG. 8 is a transverse cross-section of the drive cylinders shown in FIG. 7.
FIG. 9 is a cross-section of the means for measuring elastic recovery, mounted in the second module of the apparatus of FIG. 1.

FIG. 9 is a partial cross-section of the control means showing primarily device 37. This device comprises a capacitator 110 affixed to support 111, for example by means of screw 112, and provided with a forceps 113 for positioning the lower extremity of the test piece for which twist and/or elastic recovery are to be measured. Support 111 is vertically movable along screw 114 rotatable upon platforms 115 and 116, themselves held by two supports: a right angled sectin 117 and and a U-shaped piece 118 integral with lifting plate 11. The latter has a threaded tube or sleeve 119 for this purpose, movable in translation while controlling support 111 when the screw turns upon these support platforms, movement of the screw being controlled by means of the universal joint 121 of the stepper motor.

This device is used for the consecutive measurement of twist and of elastic recovery. In the first instance, it is used in combination with motor 34 causing forceps 36 to turn and thereby twist the thread in two successive directions, forceps 113 remaining stationary in an upward position, and in the second case, forceps 36 remain stationary while forceps 113 is lowered until thread 46 breaks. As shown in the drawing, only the forceps held by the tension sensor 110 is visible in front of mounting plate 11. Support 111 slides vertically through opening 40. The mechanical means for displacing forceps 113 is disposed behind mounting plate 11.

It is emphasized that the methods used are entirely dependent upon computerized control, from controlling the mechanical systems which initiate the process to interpreting the preliminary results, which may be accomplished immediately thereafter, in order to select which of the various methods will be applied, as well as the statistical interpretations of the results and the means of arriving at same for controlling the progression of or stopping the measurement sequence according to the data initially provided.

Moreover, statistical indexing of all the data provides graphically calculated parameters generally not possible with traditional methods, as, for example, with respect to elastic recovery: modules, capacity for work . .

. which are far more significant (and therefore more practical) in predicting product performance during use than the mere classifications of resistance and resilience previously available.

Moreover, computerized information processing allows statistical compilation not only with respect to calculating the mean, the deviation and/or the coefficient of variation, but also other statistical parameters such as, for example, coefficients of symmetry $\beta_1$ and of density distribution $\beta_2$ (Pearson's coefficient), which are indicative of the distribution in question.

The combination of the appropriate sequence of different measurements provides the advantage of supplying the information necessary for further study of particular characteristics: thus the initial automatic determination of denier furnishes a basis for calculating the voltage and automatically applying the voltage previously used.

Finally, measurement results obtained permit discussion of which type or types of quality control are necessary in a particular instance, the number of measurements to be taken and/or the degree of statistical precision required, the number of bobbins or combination thereof: number of tests per bobbin, number of bobbins, as well as the order or restrictions necessary or desired.

Obviously, it is possible to obtain data which may have been collated and processed on any kind of intermediary system: printer, memory storage, etc.

Naturally the present invention is not limited to the embodiments herein described by way of non-limiting examples, but may undergo numerous modifications and assume various forms obvious to one skilled in the art. In particular, the apparatus according to the invention is not limited to two measurement modules, but may, for example, be expanded to include a third module to determine superficial thread structure, flexibility, degree of fraying, bulk, etc.

We claim:

1. Apparatus for quality control of textile thread in which a plurality of measurements are carried out automatically by said apparatus, comprising a housing containing at least two measurement modules and a supply of at least one test piece of thread, a first of said modules being provided with means for taking measurements of at least one of denier and uniformity of linear mass for said at least one test piece of thread, the second of said modules including means for taking measurements of twist and elastic recovery properties for said at least one test piece of thread, a manipulator equipped with forcep means for automatically distributing said at least one test piece of thread to said first and second modules, when desired, means for the automatic repetition of these measurements on a series of test pieces of the same thread, means for storing the measurement results of each test in memory, central processing means for processing the results of each test for at least one of statistical compilation and memory storage, whereby the measurements obtained by one of said modules is used to calculate test parameters for the measurement performed by the other of said modules.

2. Apparatus according to claim 1, wherein the first module comprises measuring means for the determination of uniformity of linear mass, measuring means for thread denier, and a drive means for driving said at least one test piece of thread, said three means being disposed along a vertical path and being disposed to cooperate simultaneously in determining thread denier and uniformity thereof.

3. Apparatus according to claim 2, wherein the measuring means for the uniformity of linear mass comprises a double condenser having a central plate and two lateral plates defining two passageways, one of which contains the thread to be tested, as well as a connecting circuit comprising an oscillator disposed to apply an alternating voltage of opposing phases upon the lateral plates, an amplifier and a demodulator to detect variations in voltage upon the central plate and a reverse-feedback circuit comprising an analog/digital convertor and a digital/analog convertor to accommodate the disequilibrium of the connecting circuit, the demodulator being connected to said central processing means for the statistical processing and memory storage of the measurement results.

4. Apparatus according to claim 2, wherein the drive means determines a length of thread and comprises a drive cylinder controlled by a stepper drive motor and a pressure cylinder having an anti-slip surface, said pressure cylinder being equipped with means to ensure constant pressure of a peripheral surface thereof upon a peripheral surface of the drive cylinder.

5. Apparatus according to claim 4, wherein the pressure cylinder has at least one groove along an exterior peripheral edge thereof to facilitate automatic insertion of a thread between the two pressure cylinders.

6. Apparatus according to claim 1, wherein the means for measuring denier comprises a precision scale provided with a receptacle for weighing a length of thread and output means for outputting signals corresponding to the successive measurements, these signals being transmitted to the central processing means for statistical compilation and memory storage of measurement results.

7. Apparatus according to claim 1, wherein that the second module comprises a device having a stepper motor supporting a first forcep capable of being rotated in one of two directions by said stepper motor while holding one extremity of said at least one test piece of thread, and a second forcep associated with mechanical means capable of displacing the second forcep along a verticle path, when desired.

8. Apparatus according to claim 7, wherein the means for displacing the second forcep comprises a second stepper motor and a vertical screw which is caused to rotate by said second stepper motor and is connected to the second forcep to ensure its vertical displacement.

9. Apparatus according to claim 1, comprising a deflector designed to permit definition of two separate testing zones, one of which contains said at least one test piece of thread to be tested by the first module and the other of which contains said at least one test piece of thread to be tested by the second module.

10. Apparatus according to claim 1, wherein said manipulator comprising a rotating disc, a guide block mounted on two rails perpendicularly affixed to said disc so that said block is slidable along said rails, a stem slidable inside said guide block, and a manipulating arm mounted at the free end of the stem and supporting cutting forceps for lifting the threads from their preliminary positions and to move them towards the measuring means and to cut them into predetermined lengths.

11. Apparatus according to claim 1 comprising a rack formed of a body supporting a unit of stems disposed to hold bobbins of thread to be tested, suction tubes to suction these threads and to drive them through flexible tubes inside the apparatus.

12. Apparatus for quality control of textile thread in which a plurality of measurements are carried out automatically by said apparatus, comprising a housing containing at least two measurement modules and a supply of at least one test piece of thread, a first of said modules being provided with means for taking measurements of denier and uniformity of linear mass for said at least one test piece of thread, the second of said modules including means for taking measurements of twist and elastic recovery for said at least one test piece of thread, manipulator means equipped with forcep means for automatically distributing said at least one test piece of thread to said first and second modules, when desired, means for the automatic repetition of these measurements on a series of test pieces of the same thread, means for storing the measurement results of each test in memory, means for supplying at least the denier results to the second module so that test parameters for one of twist and elastic recovery can be calculated, and computerized central processing means for processing these results for at least one of statistical compilation and memory storage.

13. Apparatus according to claim 12, wherein said apparatus further comprises rack means, associated with the housing, which support bobbins of thread to be tested.

* * * * *